United States Patent
Al-Sabah et al.

(10) Patent No.: US 10,557,257 B1
(45) Date of Patent: Feb. 11, 2020

(54) SANITIZING AND SMART SMELL DETECTION DEVICE FOR HANDHELD BIDET SPRAYER AND AIR FRESHENING

(71) Applicants: Sabah Thamer Abdullah S. Al-Sabah, Safat (KW); Mohammad Salman Mohammad Salman Al-Sabah, Safat (KW); Fahad S. F. S. A. Al-Sahli, Safat (KW)

(72) Inventors: Sabah Thamer Abdullah S. Al-Sabah, Safat (KW); Mohammad Salman Mohammad Salman Al-Sabah, Safat (KW); Fahad S. F. S. A. Al-Sahli, Safat (KW)

( * ) Notice: Subject to any disclaimer, the term of this patent is extended or adjusted under 35 U.S.C. 154(b) by 0 days.

(21) Appl. No.: 16/526,179

(22) Filed: Jul. 30, 2019

(51) Int. Cl.
| | |
|---|---|
| *A61L 2/10* | (2006.01) |
| *A61L 2/22* | (2006.01) |
| *E03D 9/00* | (2006.01) |
| *E03D 9/08* | (2006.01) |

(52) U.S. Cl.
CPC ............. *E03D 9/002* (2013.01); *A61L 2/10* (2013.01); *A61L 2/22* (2013.01); *E03D 9/085* (2013.01); *A61L 2202/11* (2013.01); *A61L 2202/14* (2013.01)

(58) Field of Classification Search
CPC .............. A61L 2/10; A61L 2/22; E03D 9/085
See application file for complete search history.

(56) References Cited

U.S. PATENT DOCUMENTS

| | | |
|---|---|---|
| 5,987,659 A | 11/1999 | Cannizzaro |
| 5,991,937 A | 11/1999 | Safara |
| 7,543,339 B1 | 6/2009 | Harris |
| 2005/0246828 A1 | 11/2005 | Shirai et al. |
| 2007/0256226 A1 | 11/2007 | Pinizzotto |
| 2015/0337525 A1 | 11/2015 | Bailey |
| 2017/0172371 A1* | 6/2017 | Engesser ............... A47L 15/241 |
| 2018/0021465 A1 | 1/2018 | Dobrinsky et al. |
| 2018/0238038 A1 | 8/2018 | Pomeroy et al. |

FOREIGN PATENT DOCUMENTS

KR        101797163 B1      12/2017

OTHER PUBLICATIONS

"Handheld Bidet Sprayer for Toilet," (c) 1996-2018, Amazon.com website.

* cited by examiner

*Primary Examiner* — Sean E Conley
(74) *Attorney, Agent, or Firm* — Richard C. Litman; Nath, Goldberg & Meyer (57) ABSTRACT

A sanitizing device for a handheld bidet sprayer includes a housing for holding a handheld bidet sprayer on a spray head mount, an optical sensor used to detect the presence or absence of the sprayer in the housing, an odoriferous substance sensor used to sense odoriferous conditions or indications of a significant presence of microbes, a chemical supply holder, an ultraviolet light source, and a control module. The chemical supply holder includes at least one container of fragrance and at least one container of sanitizer. Upon sensing odoriferous conditions or indications of a significant presence of microbes, the control module causes the discharge of the sanitizer and/or fragrance.

6 Claims, 7 Drawing Sheets

SANITIZING AND SMART SMELL DETECTION DEVICE FOR HANDHELD BIDET SPRAYER AND AIR FRESHENING

BACKGROUND

1. Field

The disclosure of the present patent application relates to a sterilization device, and particularly, to a device for sterilizing a handheld bidet sprayer and smart smell detection apparatus.

2. Description of the Related Art

A bidet generally refers to a plumbing fixture that can be used for washing the genitals and anal area after using the toilet followed by air freshening process. In some instances, the bidet includes a fixture that is integrated with the toilet. In other instances, the bidet includes a separate fixture or appliance, such as a handheld bidet sprayer next to the toilet. Also, due to the manner in which the handheld bidet sprayer is used, the handheld bidet sprayer is susceptible to accumulation of microbial growth pollution. This is particularly the case when the bidet sprayer is used in a public space, such as a restaurant. Thus, a device for sterilizing a handheld bidet sprayer solving the aforementioned problems is desired.

SUMMARY

A sanitizing device for a handheld bidet sprayer includes a housing for holding a handheld bidet sprayer on a spray head mount, an optical sensor used to detect the presence or absence of the sprayer in the housing, an odoriferous substance sensor used to sense odoriferous conditions or indications of a significant presence of microbes, a chemical (perfume) supply holder, an ultraviolet light source, and a process control module. The chemical supply holder includes one or more containers of a fragrance and/or one or more containers of a chemical, and a plurality of conduits extending from the containers. Upon sensing indications of a significant presence of microbes, e.g., a fishy smell or other odoriferous conditions, the sanitizer can be discharged to sanitize the spray head and/or fragrance can be discharged to condition the air.

Sanitization of the spray head can be further provided by the ultraviolet light source. The ultraviolet light source can include an ultraviolet lamp and driver circuit for powering the ultraviolet light lamp. During a sanitation cycle, the ultraviolet light source provides surface sterilization of the handheld bidet sprayer.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

As shown in FIGS. 1-4, a sanitizing device for a handheld bidet sprayer 10 can include a housing 11 for holding a handheld bidet sprayer S on a spray head mount 12, an optical sensor 13 for detecting the presence or absence of the sprayer S in the housing 11, an optical transmitter 14, an odoriferous substance sensor 17 for sensing odoriferous conditions or indications of a significant presence of microbes, a chemical supply holder 18, an ultraviolet light source 37, and a control module 28. The housing can also include device cover 25, one or more batteries 29, and battery cover 27 with battery cover attachment 26. The UV or germicidal light source 37 is controlled by control module 28 and can be used to sanitize the device itself. In an embodiment, the one or more batteries 29 can include triple-A batteries. In an embodiment, the one or more batteries 29 includes a rechargeable battery, e.g., a Li-ion battery.

The chemical supply holder 18 stores chemical containers, conduits extending from the chemical containers, and nozzles for dispensing the respective chemicals from the conduits. The chemicals can include any suitable sanitizers and fragrances which are compatible with the device. The use of fragrances allows conditioning of the air in response to different types of odors. The sanitizer can be used to sanitize the sprayer S. In an exemplary embodiment, the chemical supply holder houses fragrance containers 21a, 21b, and one sanitizer container 22. Conduit 19a is connected to fragrance container 21a and pump 36a, conduit 19b is connected to fragrance container 21b and pump 36b, and conduit 20 is connected fragrance container 22. Upon sensing odoriferous conditions or indications of a significant presence of microbes, the control module 28 can cause the discharge of the sanitizer and/or fragrance through outlet nozzles 16a and/or 16b. Latches 23, 24 can be provided to mount chemical supply holder 18 to housing 11.

Figure 1:
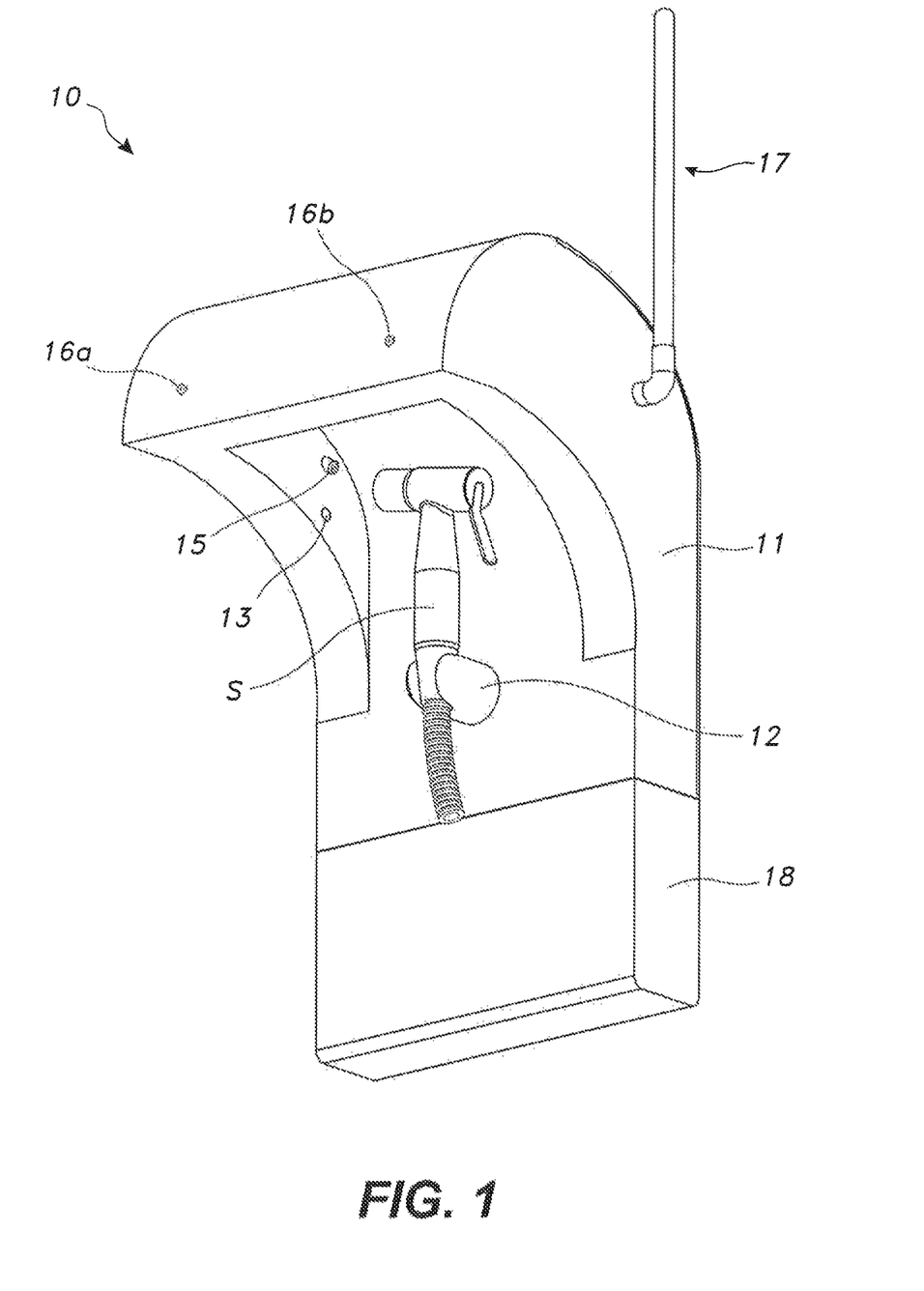
FIG. 1 is a perspective view of a sanitizing device for a handheld bidet sprayer.
Figure 2:
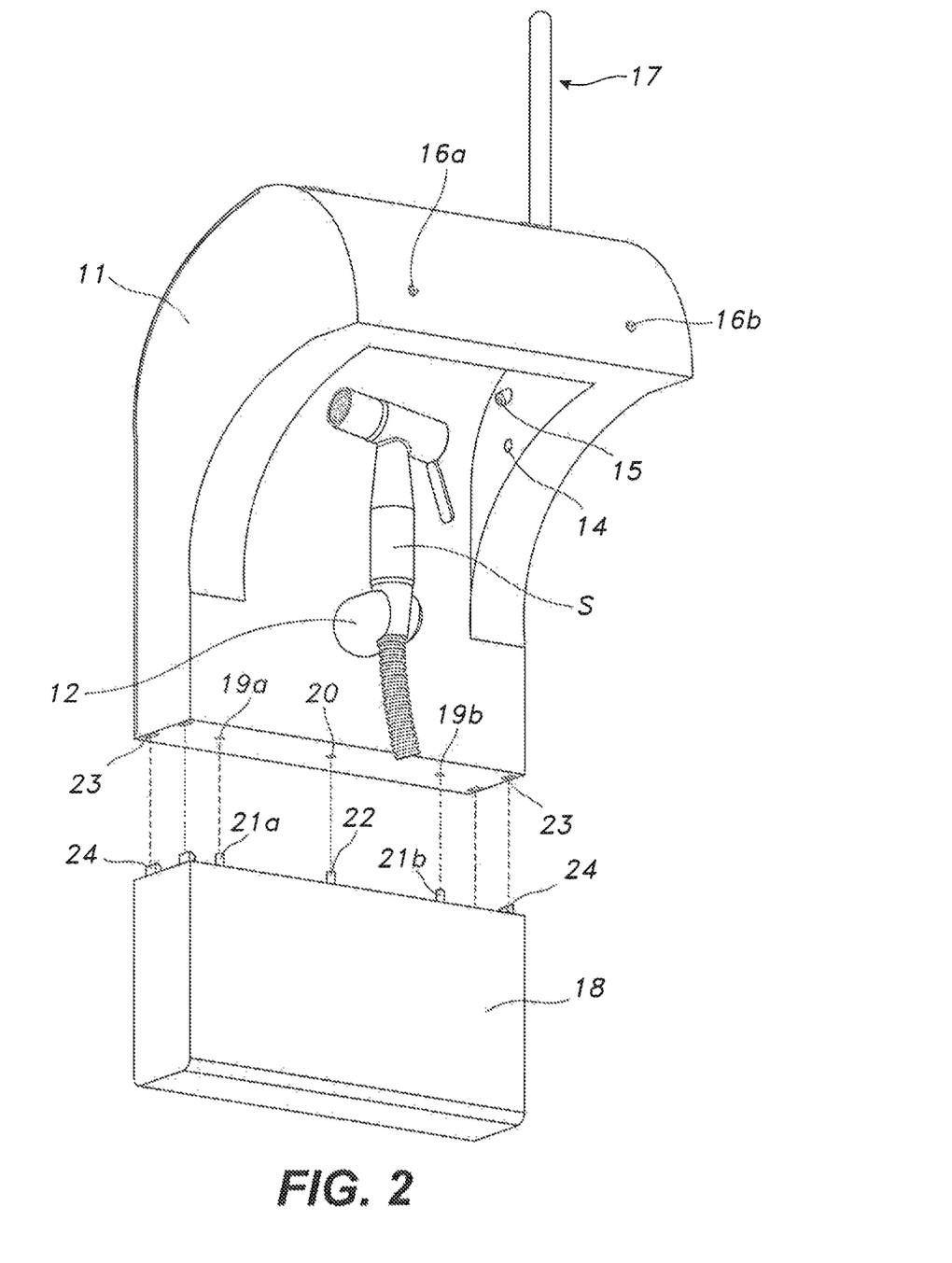
FIG. 2 is a partially exploded view of the sanitizing device for a handheld bidet sprayer.
Figure 3:
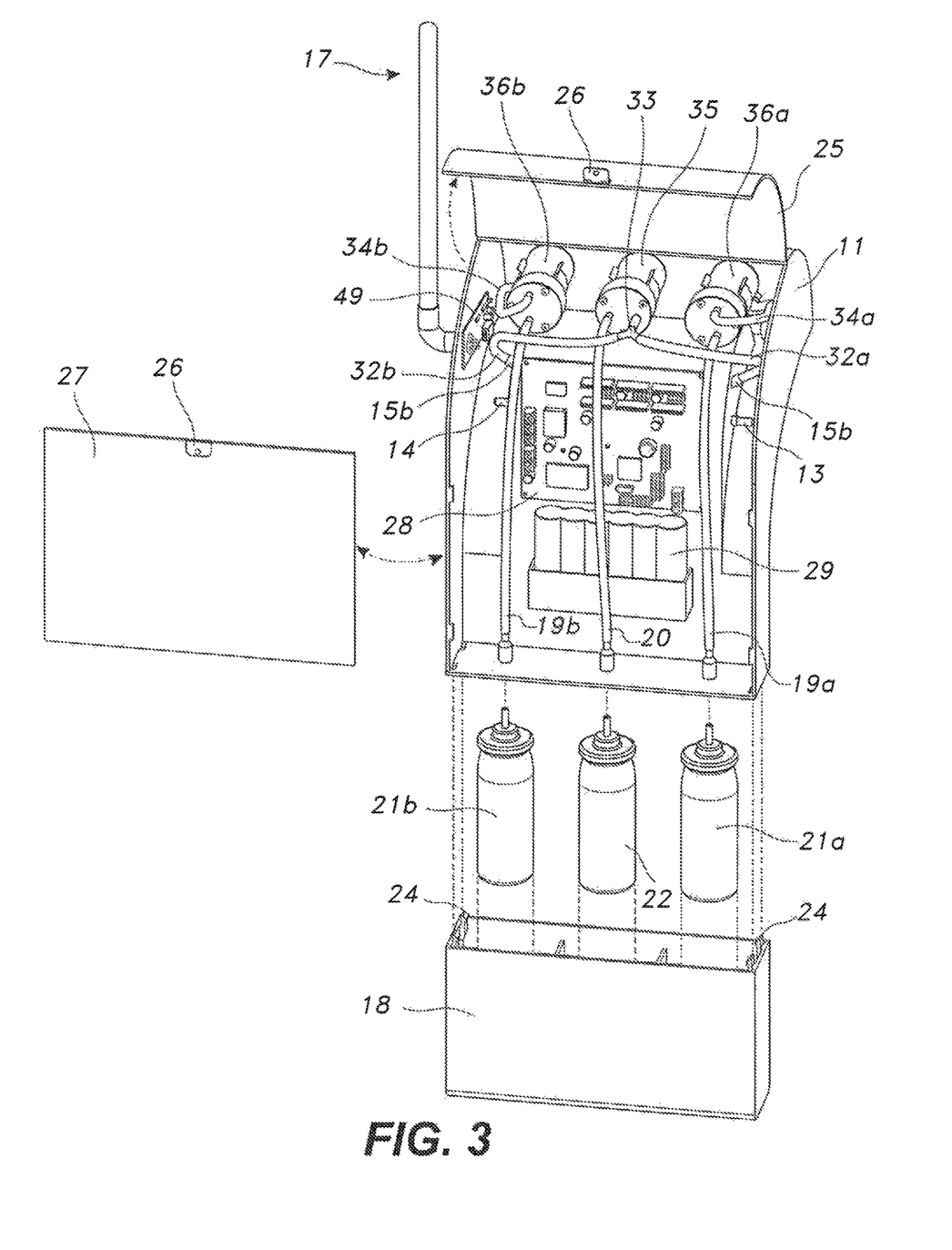
FIG. 3 is a partially exploded, partial view of an inner portion of the sanitizing device for a handheld bidet sprayer.
Figure 4:
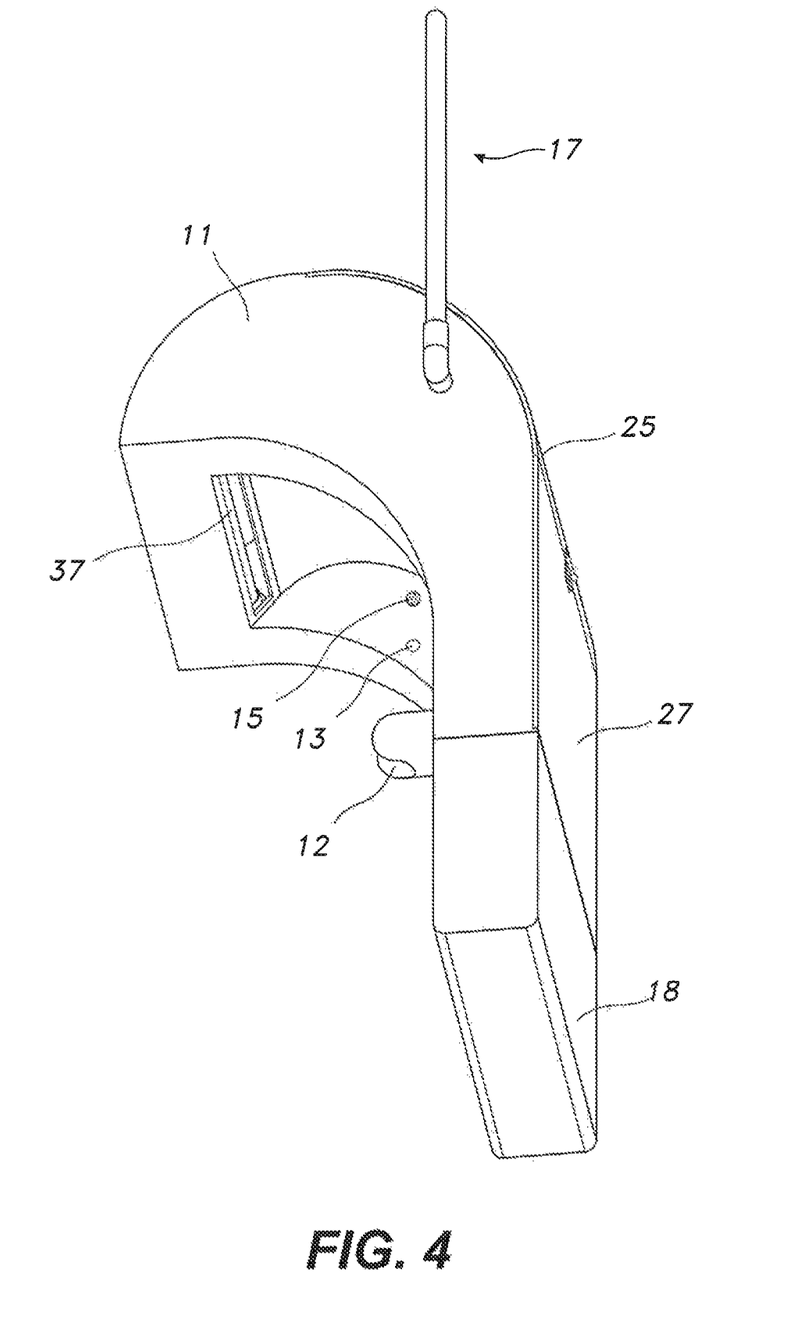
FIG. 4 is a side view of the sanitizing device for a handheld bidet sprayer, showing the ultraviolet lamp.
Figure 5:
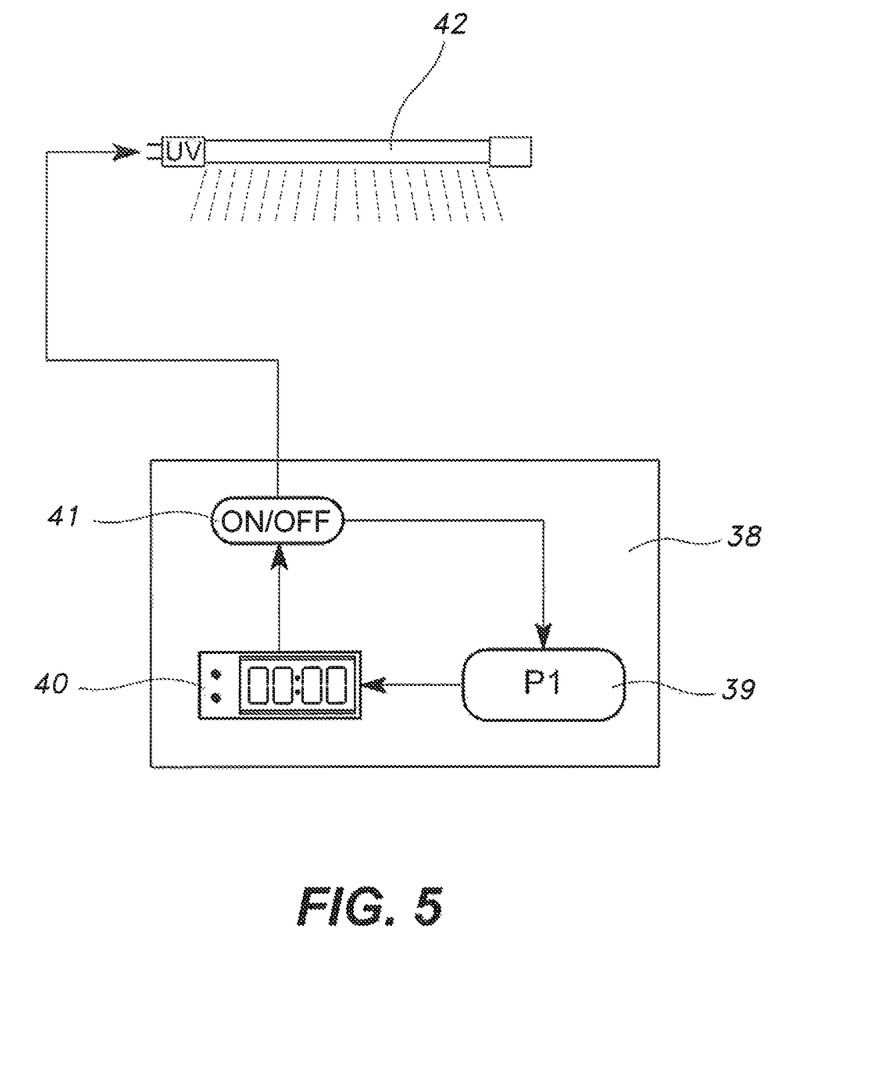
FIG. 5 is a schematic diagram showing an ultraviolet control unit of the sanitizing device for a handheld bidet sprayer.

As shown in FIG. 5, the ultraviolet light source 37 can include a sensor and control circuit 38, UV controller-power module and driver circuit 39, UV controller 40, switch 41, and UV lamp 42. The ultraviolet light can be generated as short wavelength UV light (UV-C), although anticipated wavelengths can be in the range of 10-350 nanometers, with a possibility of lower or higher wavelength UV light according to the anticipated target microbes. UV lamp 42 can be any convenient UV source, for example LED light or a germicidal light, such as a 253.7 nm germicidal light. It is further anticipated that UV lamp 42 can be configured to provide multiple wavelengths of ultraviolet light. The ultraviolet light can be directed to the sprayer S to disinfect the sprayer S.

The device 10 can be programmed to discharge fragrance through fragrance outlet nozzles 16a and 16b, according to whether a user is present, upon detection of the bidet spray S by optical sensor 13, and/or upon detection of odor by odor sensor 17.

Figure 6:
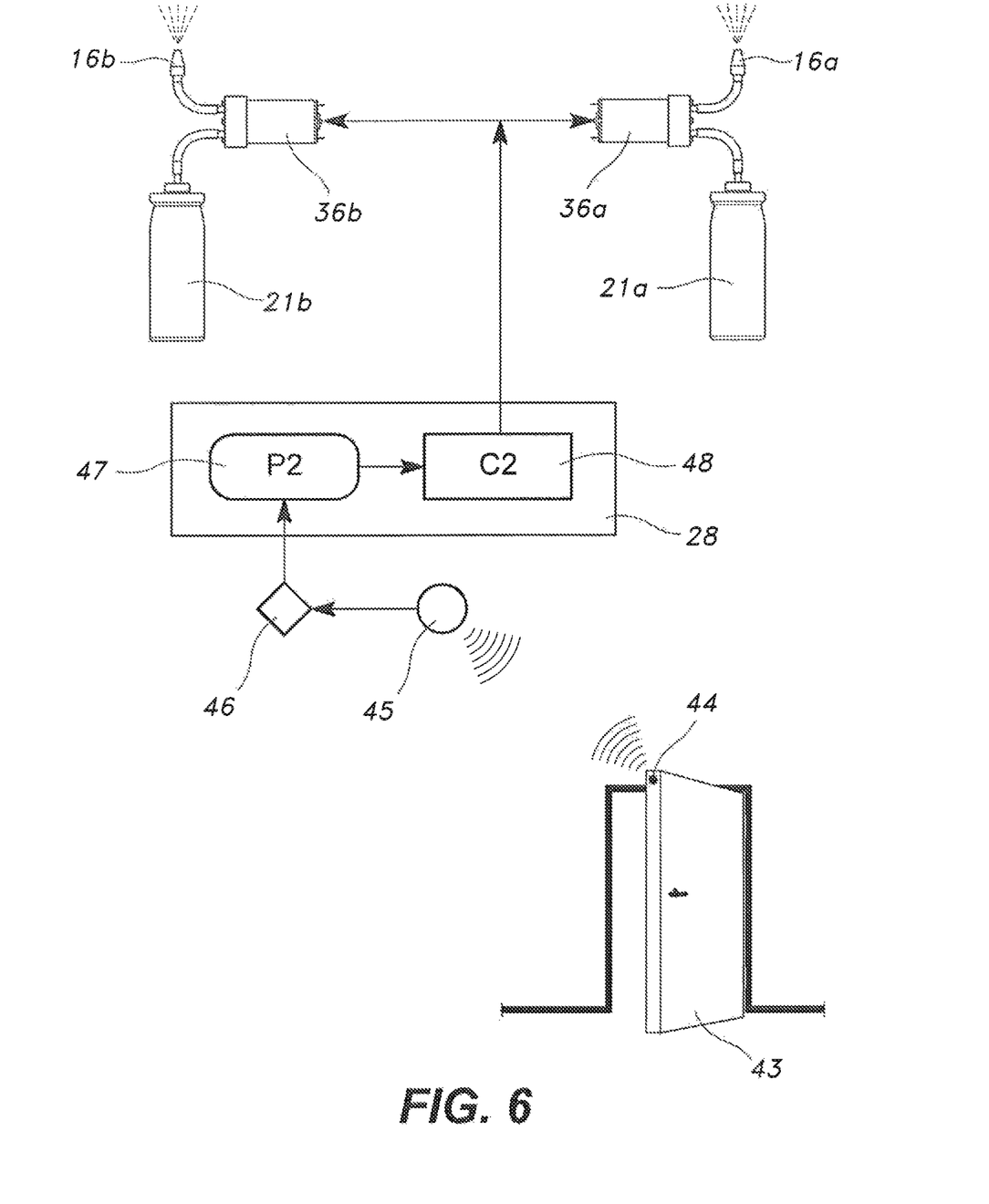
FIG. 6 is a schematic diagram showing the control module for activation of the sterilizer and odor detection device in response to a user entering or leaving the bath or toilet facility.
Figure 7:
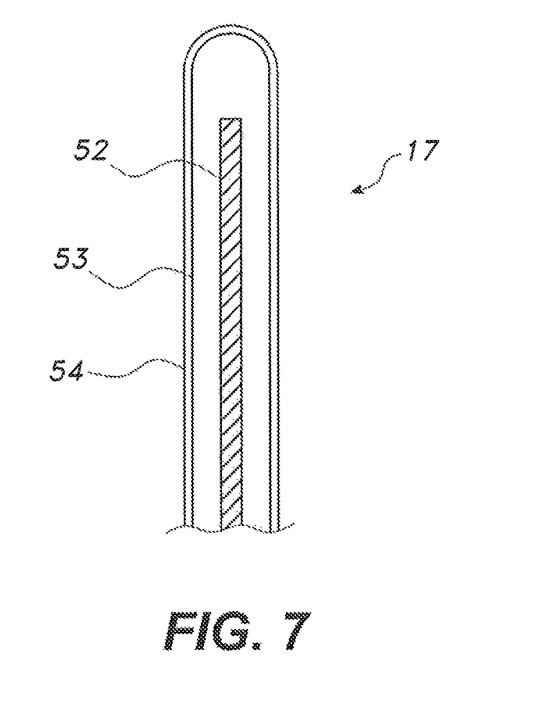
FIG. 7 is a schematic diagram of the sanitizing device for a handheld bidet sprayer, showing details of the odor sensor.

FIG. 7 is a schematic diagram showing details of a non-limiting example of the construction of the odor sensor 17 depicted in FIGS. 1-4. The odor sensor 17 includes internal copper chemistry sensor or detector 52, and a hollow porous rod 54 coated with moisture absorbance material 53. The rod 54 can be, for example, a stainless steel rod. Moisture absorbance material 53 can have an affinity for large molecules associated with odors, including molecules which are carried by moisture. FIG. 6 is a schematic diagram showing activation of the sterilizer and odor detection device in response to a user entering or leaving the bath or toilet facility. This allows general activation, but also limits sensing of odor conditions to times when the toilet or bath space is occupied. The large molecules trapped by the absorbance material 53 can be extracted by the rod 54 and detected by the sensor 52. The sensor 52 can transmit a signal to processor 47 of control unit 28, and as a result, controller 48 of control unit 28 can cause release of the appropriate chemicals. Presence detection transmitter 44 and sensors 45 and 46 similarly transmit signals to the processor 47 and controller 48, which are part of control unit 28. Controller 48 can cause sterilizer or fragrance to be discharged to treat bidet sprayer S. UV light can be projected by UV light source 37 to irradiate bidet sprayer S. In addition or alternatively, optical sensor 13 can be used by control unit 28 to sense the presence or removal of bidet sprayer S. Once the bidet sprayer S is installed on the mount, the sensor 13 can transmit infrared waves to the control unit, which in turn will activate the pump to dispense the sanitizer. The device 10 can be configured to dispense sanitizer or fragrance for a predetermined amount of time once the pump is activated.

Other configurations can be used for moisture sensing, such as are commonly found on gas detectors and solid state alcohol sensors. Although not shown, the device 10 may further include one or more brushes for scrubbing the sprayer S and/or one or more indicators to indicate that the chemical containers need to be refilled.

It is to be understood that the sanitizing device for handheld bidet sprayer is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A sanitizing device for a handheld bidet sprayer, comprising:
    a housing;
    a spray head mount on the housing;
    a control module within the housing;
    an optical sensor affixed to the housing, the optical sensor configured to detect the presence or absence of a bidet sprayer on the spray head mount;
    an odoriferous substance sensor affixed to the housing, the sensor configured to sense odoriferous conditions or indications of a significant presence of microbes; and
    a chemical supply holder within the housing, the chemical supply holder comprising:
        at least one container of sanitizer;
        at least one container of fragrance;
        a plurality of pumps;
        a plurality of discharge output nozzles; and
        a plurality of pump supply conduits, each conduit extending between a respective pump and nozzle; wherein the plurality of pumps are configured to extract the sanitizer and fragrance from respective ones of the containers of sanitizer and fragrance and discharge the sanitizer and fragrance from the discharge output nozzles.

2. The sanitizing device as described in claim 1, wherein the housing further comprises:
    an ultraviolet light source;
    an ultraviolet lamp;
    a driver circuit for powering the ultraviolet light source, whereby, during a sanitation cycle, the ultraviolet light source provides surface sterilization of a handheld bidet sprayer.

3. The sanitizing device as described in claim 1, wherein the odoriferous substance sensor comprises:
    an internal copper chemistry detector having a surface coating moisture absorbance material with an affinity for large molecules associated with odors; and
    a hollow porous rod coated with moisture absorbance material having an affinity for large molecules associated with odors,
    wherein the large molecules associated with odors comprises molecules carried by moisture.

4. A handheld bidet system, comprising:
    a housing;
    a spray head mount on the housing;
    a handheld bidet having a sprayer removably mounted on the spray head mount;
    a control module within the housing;
    an optical sensor affixed to the housing, the optical sensor configured to detect the presence or absence of a bidet sprayer on the spray head mount;
    an odoriferous substance sensor affixed to the housing, the sensor configured to sense odoriferous conditions or indications of a significant presence of microbes; and
    a chemical supply holder within the housing, the chemical supply holder comprising:
        at least one container of sanitizer;
        at least one container of fragrance;
        a plurality of pumps;
        a plurality of discharge output nozzles; and
    a plurality of pump supply conduits, each conduit extending between a respective pump and nozzle; wherein the plurality of pumps are configured to extract the sanitizer and fragrance from respective ones of the containers of sanitizer and fragrance, and discharge the sanitizer and fragrance from the discharge output nozzles.

5. The handheld bidet system as described in claim 4, wherein the housing further comprises:
    an ultraviolet light source;
    an ultraviolet lamp;
    a driver circuit for powering the ultraviolet light source, whereby, during a sanitation cycle, the ultraviolet light source provides surface sterilization of a handheld bidet sprayer.

6. The handheld bidet system as described in claim 4, wherein the odoriferous substance sensor comprises:
    an internal copper chemistry detector having a surface coating moisture absorbance material having an affinity for large molecules associated with odors; and
    a hollow porous rod coated with moisture absorbance material having an affinity for large molecules associated with odors, wherein the large molecules associated with odors comprises molecules carried by moisture.

* * * * *